(12) United States Patent
Mazar et al.

(10) Patent No.: US 7,333,853 B2
(45) Date of Patent: Feb. 19, 2008

(54) IMPLANTABLE MEDICAL DEVICE HAVING A CONTROLLED DIAGNOSTIC FUNCTION

(75) Inventors: Scott Thomas Mazar, Inver Grove Heights, MN (US); Bruce H. Kenknight, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 626 days.

(21) Appl. No.: 10/305,548

(22) Filed: Nov. 26, 2002

(65) Prior Publication Data

US 2004/0102816 A1   May 27, 2004

(51) Int. Cl.
*A61N 1/00* (2006.01)
(52) U.S. Cl. .............................. 607/2; 607/115; 607/16; 607/117
(58) Field of Classification Search .................. 607/16, 607/34
See application file for complete search history.

(56) References Cited

U.S. PATENT DOCUMENTS

| | | | |
|---|---|---|---|
| 3,057,356 A | 10/1962 | Greatbatch | |
| 4,390,022 A | 6/1983 | Calfee et al. | |
| 4,523,595 A | 6/1985 | Zibell | |
| 5,282,837 A * | 2/1994 | Adams et al. | 607/5 |
| 5,350,407 A | 9/1994 | McClure et al. | |
| 5,464,432 A * | 11/1995 | Infinger et al. | 607/5 |
| 5,527,345 A * | 6/1996 | Infinger | 607/4 |
| 5,645,569 A * | 7/1997 | Ayers | 607/4 |
| 5,746,697 A | 5/1998 | Swedlow et al. | |
| 6,016,448 A | 1/2000 | Busacker et al. | |
| 6,038,476 A | 3/2000 | Schwartz | |
| 6,073,049 A | 6/2000 | Alt et al. | |
| 6,363,280 B1 * | 3/2002 | Mouchawar et al. | 607/16 |

FOREIGN PATENT DOCUMENTS

WO   WO 01/43823 A1   6/2001

\* cited by examiner

*Primary Examiner*—Angela D. Sykes
*Assistant Examiner*—Brian T. Gedeon
(74) *Attorney, Agent, or Firm*—Schwegman, Lundberg & Woessner, P.A.

(57) ABSTRACT

Methods and systems for providing an implantable medical device with a controlled diagnostic function adapted to convert from a monitoring mode to a therapeutic mode upon sensing an actionable cardiovascular event are disclosed. A preferred embodiment uses an interactive control module to selectively control a plurality of gated circuits that turn the sensing, therapeutic and communications functions of the device on and off to conserve battery power and extend the life of the device. Some embodiments of a system disclosed herein also can be configured as a component of an Advanced Patient Management System that helps better monitor, predict and manage chronic diseases.

19 Claims, 4 Drawing Sheets

IMPLANTABLE MEDICAL DEVICE HAVING A CONTROLLED DIAGNOSTIC FUNCTION

TECHNICAL FIELD

The present device relates generally to implantable cardiovascular medical devices and particularly, but not by way of limitation, to such a device that can diagnose patient health by periodically monitoring patient health and converting from a monitoring mode to a therapeutic mode upon sensing a cardiovascular event.

BACKGROUND

When functioning properly, the human heart maintains its own intrinsic rhythm based on physiologically-generated electrical impulses. It is capable of pumping adequate blood throughout the body's circulatory system. Each complete cycle of drawing blood into the heart and expelling it is referred to as a cardiac cycle.

However, some people have abnormal cardiac rhythms, referred to as cardiac arrhythmias. Such arrhythmias result in diminished blood circulation. Arrhythmias can occur in the upper chambers of the heart—the atria, or the lower chambers of the heart—the ventricles. However, ventricular arrhythmias present the most serious health risk as they can lead to rapid death from the lack of circulation. Arrhythmias can be subdivided further into specific conditions of the heart that represent vastly different manifestations of abnormal cardiac rhythm. These conditions are bradycardia, or a slow heartbeat, and tachycardia, or a fast heart beat.

One mode of treating a cardiac arrhythmia uses an implantable medical device. Such implantable medical devices include pacemakers, also referred to as pacers, and defibrillators. The traditional use of a pacemaker is to treat a person with bradycardia. In other words, pacemakers help speed up the cardiac cycle of a person whose heart beats too slowly. Pacers accomplish this by delivering timed sequences of low energy electrical stimuli, called pace pulses, to the heart. Such stimuli are delivered via an intravascular lead wire or catheter (referred to as a "lead") having one or more electrodes disposed in or about the heart.

In comparison to a pacemaker, an implanted defibrillator applies a much stronger electrical stimulus to the heart. This is sometimes referred to as a defibrillation countershock, also referred to simply as a "shock." The shock changes ventricular fibrillation to an organized ventricular rhythm or changes a very rapid and ineffective cardiac rhythm to a slower, more effective rhythm. Defibrillators help treat cardiac disorders that include ventricular fibrillation, ventricular tachycardia, atrial fibrillation, and atrial flutter. These inefficient or too rapid heartbeats reduce the pumping efficiency of the heart and thereby diminish blood circulation. The countershock delivered by the defibrillator interrupts the tachyarrhythmia, allowing the heart to re-establish a normal rhythm for the efficient pumping of blood.

Another mode of treating a cardiac arrhythmia uses drug therapy. Drugs are often effective at restoring normal heart rhythms. Modern implantable medical devices can be configured to release drugs through specialized leads or a pumping device. Steroids are commonly administered in this manner to suppress inflammation of the heart wall. However, with continuing advances in pharmaceutical research, powerful anti-arrhythmic drugs may also be administered through an implantable medical device.

An implantable medical device also can be configured to include an accelerometer. A tiny crystal sensor inside the device detects body movement and signals the device to adjust pacing of the heart up or down according to the wearer's activity. This technology has been further refined so that modern implantable medical devices can mimic the heart's natural rhythm even more closely by adjusting the rhythm according to a person's activity level. Modern implantable medical devices also can separately sense and coordinate the contractility of both the upper (atria) and lower (ventricles) chambers of the heart and serve as dual pacer/defibrillators, drug delivery devices, and as a component of a comprehensive patient management system for predictive management of patients with chronic disease.

Modern implantable medical devices are becoming smaller (½ the size) and smarter than earlier devices and can last much longer. With the recent introduction of "mode switching," modern devices can now, for example, recognize an abnormally fast heart rate in the upper chamber of the heart and react by automatically changing the therapy the device delivers. This feature allows the device to deliver the most appropriate therapy. Modern implantable medical devices also can collect information and store it until the next clinic visit. Some devices also make follow-up easier by storing patient data directly into the memory of the device (such as name, diagnosis, doctor).

However, by tasking the implantable medical device to do more, the demands on the device's power supply, typically a lithium-iodine battery, increase, such that the device may need to be replaced more often. In order for an implantable medical device to serve multiple functions without having to be frequently replaced, the battery life, and hence, the useful life of the device, must be extended. This can be accomplished by duty cycling the device's major subsystems. In other words, the device is on and using power only during specific periods to help conserve battery power.

Thus, for these and other reasons, there is a need for an implantable medical device that can serve multiple therapeutic purposes for many years without having to replace the device on more than a few occasions, if ever, during the patient's lifetime.

SUMMARY

According to one aspect of the invention, there is provided a method and device for the controlled diagnosis and treatment of a cardiovascular event using a convertible implantable medical device with an extendable battery life. A cardiovascular event within the context of the invention comprises an arrhythmic event.

The convertible implantable medical device described herein comprises subsystems that perform specific functions. Those functions comprise a sensing function, a therapy function and a communications function. Each function can be selectively controlled by a separate control, or combined control and analysis module that opens and closes gated circuits. Gated circuit S controls an interactive sensing module that activates the sensing function. Gated circuit T controls an interactive therapy module that activates the therapy function, and gated circuit C controls an interactive communications module that activates the communications function. When a gated circuit is closed, it completes an electrical circuit with the power source and the module it controls and activates the function of that module.

In one embodiment, the device is configured to duty cycle from active (on) to inactive (off or dormant) states through the use of gated circuit S. When the control and analysis module closes gated circuit S, the circuit is complete and the sensing module is activated to perform the sensing function.

When gated circuit S is open (off), the sensing module is inactive. By way of non-limiting example only, a single duty cycle might be timed by gated circuit S being closed for 10 seconds out of every minute. When gated circuit S is closed, the sensing module monitors and senses cardiovascular function. If the sensing module senses a cardiovascular event requiring intervention, the device converts from monitoring mode to therapeutic mode. Therapy can comprise electrical stimulation or chemotherapy. Duty cycling the device in this manner conserves power without compromising patient health. When the device is dormant, the power demand on the battery is minimal. However, because the dormant state interval is relatively short, a sustained or persistent cardiovascular event that is sensed when the sensing module is activated would likely be diagnosed and treated before it becomes life threatening.

In another embodiment, the control and analysis module controls gated circuits S and T. When gated circuit T is closed (on), the circuit is complete and the therapy module is activated to perform the therapy function. When gated circuit T is open (off), the therapy module is inactive. By way of non-limiting example only, gated circuit S can be permanently closed (on) to permanently activate the sensing module and function. When the sensing module senses an actionable cardiovascular event, gated circuit T switches on the therapy module temporarily. In this embodiment, the device can serve as a defibrillator and post-detection guardian by allowing the device to respond instantly to an acute event like cardiac fibrillation, which is potentially life threatening.

In yet another embodiment, gated circuit S and the sensing module can again be permanently on to sense a cardiovascular event requiring intervention. However, by way of non-limiting example only, when the sensing module senses an actionable cardiovascular event, gated circuit T and the therapy module is activated permanently and is available to provide continuous therapy. In this embodiment, the device can serve as a pacer by allowing the device to provide continuous therapy for a chronic cardiac condition like bradycardia.

In a further embodiment, the device comprises a control and analysis module, a sensing module, a therapy module and a communications module. The control and analysis module directs the closed and open states of gated circuits S, T and C, which in turn activate the sensing, therapy and communications modules respectively. The selective activation of the modules and their functions through the gated circuits controls the duty cycle of the device. By way of non-limiting example only, when gated circuit S is closed, the sensing module is activated and monitors and senses patient health using predefined cardiovascular parameters. If the sensing module senses a cardiovascular event, it relays that information to the control and analysis module. The control and analysis module analyzes and diagnoses the cardiovascular event to determine if therapeutic intervention is necessary. If so, the control and analysis module closes gated circuit T to activate the therapy module, which delivers an appropriate course of therapy. At any time, the control and analysis module may close gated circuit C, which activates the communications module. The communications module communicates the diagnosed and treated cardiovascular event to the control and analysis module to control further operation of the device and/or to a data accessible patient management system. Such communicated cardiovascular data may be used as data points in post-myocardial infarction randomized controlled trials (RCTs).

In a preferred embodiment of the convertible, implantable medical device, the device has diagnostic and therapeutic functions and is powered by a battery adapted to power operation of the device for at least 7 years. Lithium-based batteries may be employed to satisfy the embodiment wherein the device is powered for at least 7 years. As implantable medical device battery technology develops, batteries comprising other than lithium may be employed to satisfy the embodiment wherein the device is powered for at least 7 years. The device also comprises an interactive control and analysis module adapted to analyze and diagnose an arrhythmic cardiovascular event and selectively control a plurality of gated circuits S, T and C that turn the functions of the device on and off by closing and opening the gated circuits. By selectively closing and opening the gated circuits, the operation of the device can be duty cycled between active, partially active or inactive states to conserve power. When duty cycled in this manner, the device is adapted to monitor and assess patient health within ranges of nominal to maximal vigilance. In this embodiment, the interactive control and analysis module, which is always active, is coupled to the interactive sensing module that is adapted to sense an arrhythmic cardiovascular event. The interactive control and analysis module also is coupled to the interactive therapy module adapted to deliver an appropriate course of therapy. Therapy can be in the form of electrical stimuli or chemotherapy or a combination of both. The interactive control and analysis module is further coupled to the interactive communications module that communicates data reflecting the sensed, analyzed and diagnosed arrhythmic cardiovascular event and delivered therapy to control further operation of the device. The interactive communications module also may communicate data reflecting a record of the diagnosed and treated cardiovascular event to an externally accessible patient management system. In the preferred embodiment, the device offers the most flexibility in controlling the diagnosis and treatment of a cardiovascular event in a prophylactic manner while simultaneously conserving battery power.

The various embodiments described above are provided by way of illustration only and should not be construed to limit the invention. Those skilled in the art will readily recognize various modifications and changes that may be made to the present invention without following the example embodiments and applications illustrated and described herein, and without departing from the true spirit and scope of the present invention, which is set forth in the following claims.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

In the following detailed description, reference is made to the accompanying drawings that form a part hereof, and in which are shown by way of illustration specific embodiments or examples. These embodiments may be combined, other embodiments may be utilized, and structural, logical, and electrical changes may be made without departing from the spirit and scope of the present invention. The following detailed description is, therefore, not to be taken in a limiting sense, and the scope of the present invention is defined by the appended claims and their equivalents.

The present method and device are described with respect to an implantable cardiovascular medical device that is adapted to periodically monitor patient health and convert from monitoring mode to therapeutic mode upon sensing a cardiovascular event requiring medical intervention. In this way, the device's diagnostic function is controlled and the therapy it provides is initially prophylactic. The periodicity of monitoring and/or providing therapy is referred to as a duty cycle. The term "duty cycle" or "duty cycling" refers to the process of configuring the device to successively cycle from active (on) to inactive (off or dormant) states as a way to effectively monitor patient health while simultaneously conserving battery power. The convertible, implantable medical device also can be integrated with an "Advanced Patient Management" system. The term "patient management" refers to the process of creating and collecting patient specific information, storing and collating the information, and generating actionable recommendations to enable the predictive management of patients with chronic disease. The terms "gated" or "gated circuit" refer to the process of gating an electrical circuit so said circuit can be selectively powered.

Figure 1:
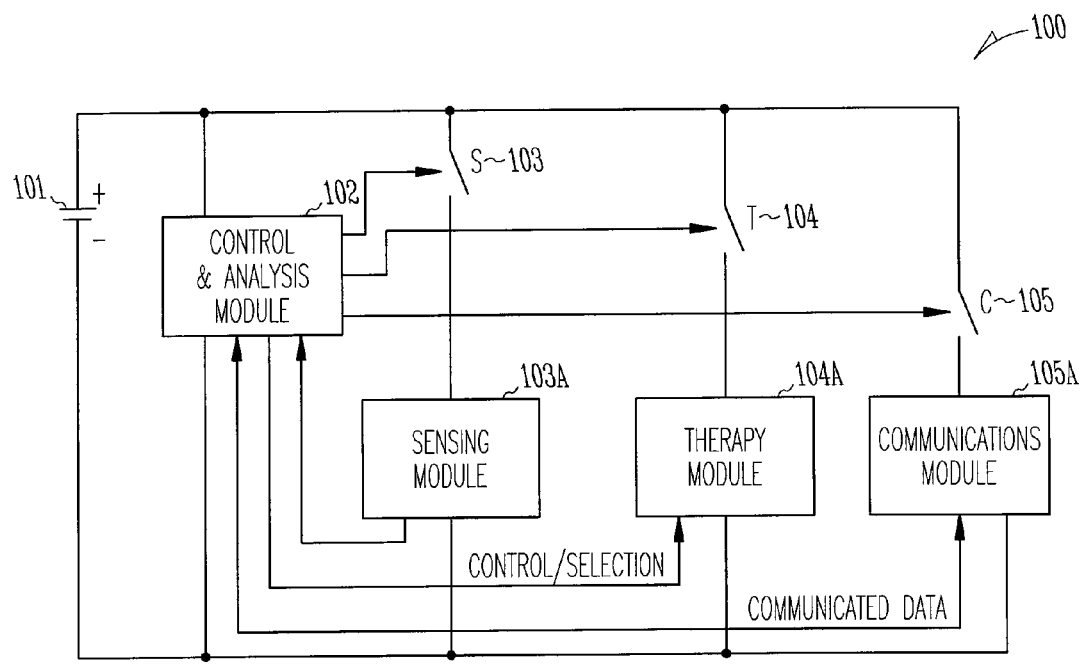
FIG. 1 is a schematic/block diagram illustrating generally, among other things, the modular subsystems of the convertible, implantable cardiovascular medical device with a controlled diagnostic function of the present invention.

FIG. 1 is a schematic/block diagram illustrating generally the modular subsystems of a convertible, implantable medical device 100 having controlled diagnostic, therapeutic and communications functions. The device 100 is powered by a battery power source 101 adapted to power operation of the device for at least 7 years. In one embodiment, such a battery power source 101 may comprise a lithium-based battery. Those of skill in the art appreciate that other types of long-lasting batteries may be used to satisfy an embodiment of the device.

As further shown in FIG. 1, the device also comprises an interactive control and analysis module 102 adapted to analyze and diagnose an arrhythmic cardiovascular event. The arrhythmic cardiovascular event can be a bradycardic or tachycardic event and can be localized in either the atria or the ventricles or both. The interactive control and analysis module 102 also controls a plurality of duty cycles that successively turn the functions of the device on and off. The duty cycles can be triggered by fixed or variable parameters.

In one embodiment, as generally illustrated in FIG. 1, a fixed duty cycle can be set by timing gated circuit S 103 to continuously cycle from active to inactive states in intervals less than 60 minutes. By way of non-limiting example only, gated circuit S 103 may be closed for an interval of 5 seconds out of every minute —5 seconds being roughly the time it takes for a human heart to complete 5 cardiac cycles. By way of further non-limiting example only, gated circuit S 103 also may be timed to duty cycle to the off state for no more than 30 seconds. When gated circuit S 103 is active, it activates sensing module 103a to sense a cardiovascular event. If sensing module 103a detects a cardiovascular event requiring intervention, sensing module 103a communicates with the interactive control and analysis module 102, which in turn closes gated circuit T 104 to activate therapy module 104a to deliver an appropriate course of therapy. At any time, the interactive control and analysis module 102 may close gated circuit C 105 to activate communications module 105a to communicate the sensed and analyzed cardiovascular event and delivered therapy data to the interactive control and analysis module 102 or an external system. By duty cycling the device in this manner, the battery life of the device is greatly conserved and can be predicted more accurately. This minimizes the number of times the device needs to be replaced, if any, during the lifetime of the patient.

In another embodiment, as again generally illustrated in FIG. 1, gated circuit S 103 can be configured to continuously cycle from active to inactive states based on a number of cardiac cycles. By way of non-limiting example only, the number of cardiac cycles that gated circuit S 103 is closed, thereby activating sensing module 103a, can be 3 cardiac cycles. In an alternative variation of this embodiment, gated circuit S 103 is closed for a physiologically or technologically appropriate time interval. A technologically appropriate time may be the time it takes the control and analysis module 102 or other analytical component to analyze and recognize a cardiovascular event requiring therapeutic intervention. Again, when gated circuit S 103 is closed, it activates sensing module 103a, which upon sensing a cardiovascular event requiring intervention, relays that information to the interactive control and analysis module, which in turn activates therapy module 104a by closing gated circuit T 104. As always, the interactive control and analysis module 102 may activate the communications module 105a by closing gated circuit C 105. In another embodiment, the gated circuit S 103 is closed to activate the sensing module 103a to sense a cardiovascular event and opened to deactivate the sensing module 103a to conserve power if no cardiovascular event is sensed.

In yet another embodiment generally illustrated in FIG. 1, a variable duty cycle of the therapeutic function might be accomplished by selectively controlling gated circuits S 103 and T 104. In this embodiment, gated circuit S 103 is always closed to permanently activate sensing module 103a for detection of a cardiovascular event. If sensing module 103a senses a cardiovascular event requiring intervention, it relays that information to the control and analysis module 102, which in turn closes gated circuit T 104 to activate therapy module 104a. In this embodiment, gated circuit T 104 and therapy module 104a can be activated temporarily or permanently.

When gated circuit T 104 is temporarily closed, it temporarily activates therapy module 104a. Therapy module 104a is available to deliver appropriate therapy should sensing module 103 detect another cardiovascular event requiring intervention. In this embodiment, the implantable medical device can serve as a defibrillator and a post-detection guardian against a subsequent, but temporally proximate cardiovascular event. When gated circuit T 104 permanently activates therapy module 104*a*, therapy module 104*a* provides continuous therapy. In this embodiment, the implantable medical device can serve as a pacer for treatment of post-implant heart block development or other chronic ailments requiring constant pacing of the heart. In either the temporary or permanent activation of therapy module 104*a*, the interactive control and analysis module 102 may activate the communications module 105*a* by closing gated circuit C 105.

Figure 2:
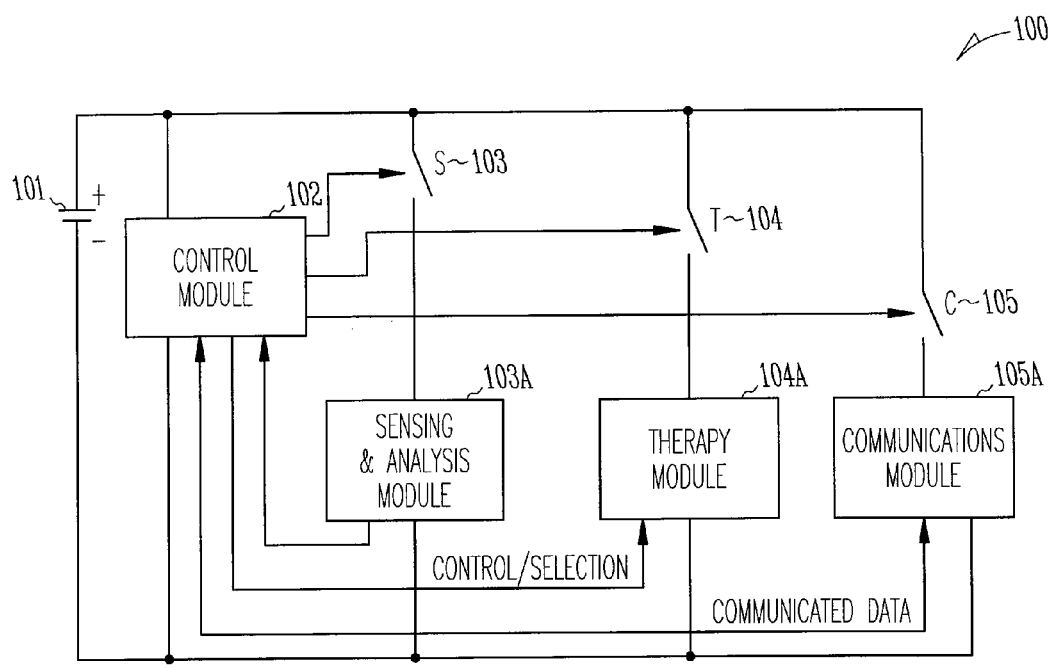
FIG. 2 is a schematic/block diagram illustrating generally, among other things, another embodiment of the modular subsystems of the convertible, implantable cardiovascular medical device with a controlled diagnostic function of the present invention.

FIG. 2 is a schematic/block diagram illustrating generally, among other things, another embodiment of the modular subsystems of a convertible, implantable medical device 100 having controlled diagnostic, therapeutic and communications functions. In this embodiment, which in most functional respects is identical to FIG. 1, the sensing module 103*a* not only performs the sensing function, but also the analysis function.

Figure 3:
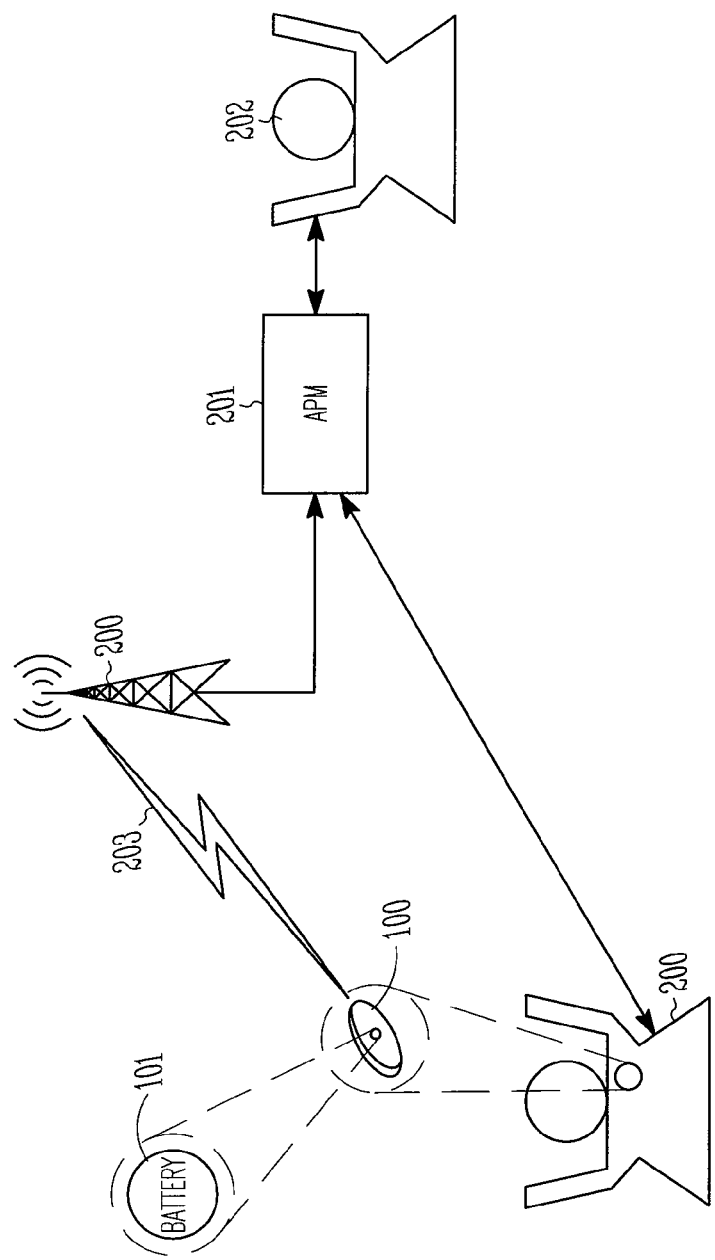
FIG. 3 is a schematic/block diagram illustrating generally, among other things, another embodiment of the convertible, implantable cardiovascular medical device with a controlled diagnostic function of the present invention.

FIG. 3 is a schematic/block diagram illustrating generally an embodiment of a convertible, implantable medical device 100 having controlled diagnostic and therapeutic functions implanted within a patient 200. The device 100 is powered by a long-lasting battery power source 101 adapted to power operation of the device for at least 7 years. The implantable medical device 100 is adapted to electronically communicate 203 a record of a diagnosed cardiovascular event and delivered therapy to an external device like an Advanced Patient Management system 201 that is accessible by the patient 200 and/or a physician or other clinician 202. Those of skill in the art appreciate that electronic communication with the APM may be accomplished by the use of various wired or wireless technologies.

Figure 4:
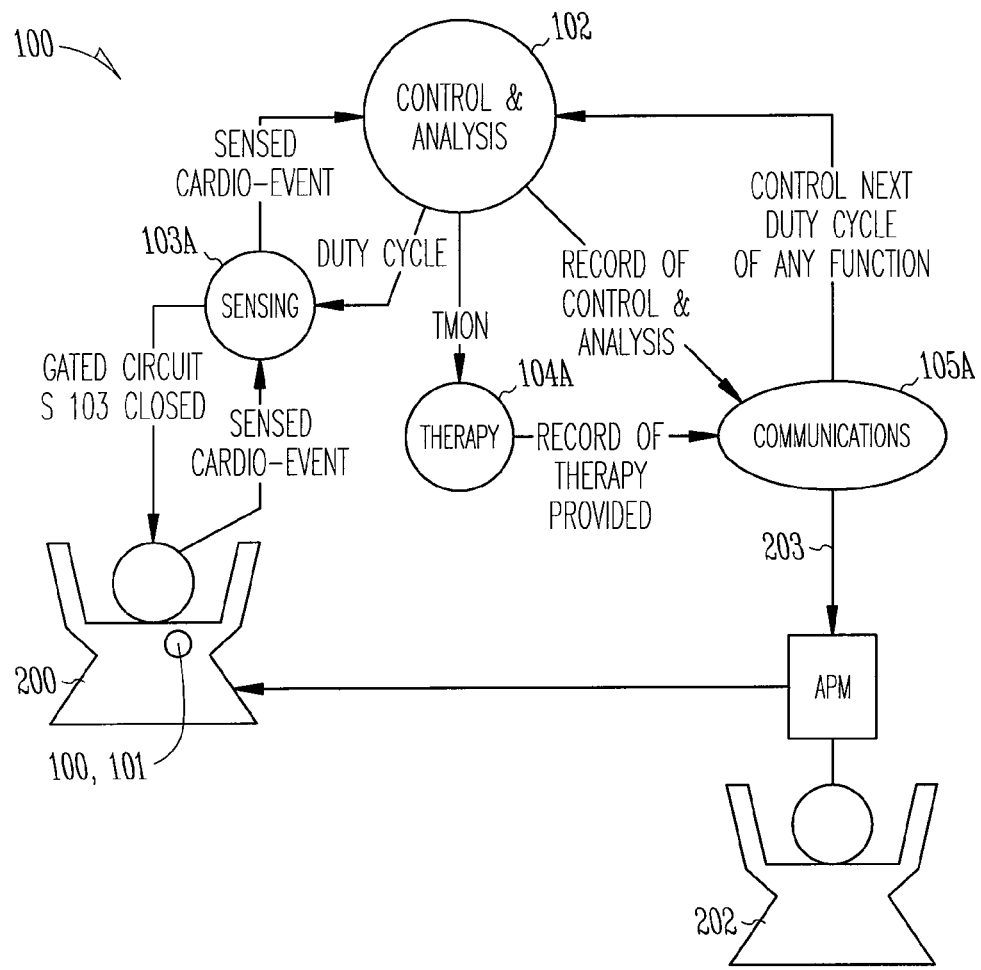
FIG. 4 is a state diagram illustrating generally, among other things, the functions and activation sequences of the subsystems of the convertible, implantable cardiovascular medical device with a controlled diagnostic function of the present invention.

FIG. 4 is a state diagram illustrating generally, among other things, the functions and activation sequences of the subsystems of the convertible, implantable medical device 100 comprising a control and analysis function 102, a sensing function 103*a*, a therapeutic function 104*a* and a communications function 105*a*. The modules are coupled in such a manner that the specific functions of the modules can be selectively duty cycled to a variety of active and inactive states. The control and analysis module 102 controls the duty cycles and functions of the modules by selectively closing gated circuits S 103, T 104 and C 105 as shown in FIG. 1. Gated circuit S 103 activates the sensing module 103*a*, which performs the sensing function. Gated circuit T 104 activates the therapy module 104*a*, which performs the function of delivering therapy. Gated circuit C 105 activates the communications module 105*a*, which performs the communications function. In an embodiment shown in FIG. 3, when gated circuit S 103 is closed, the sensing module 103*a* monitors and senses patient health using predefined cardiovascular parameters. Those parameters can be indexed against standard population data or customized according to a patient's 200 unique health profile. If the sensing module 103*a* senses a cardiovascular event, the control and analysis module 102 analyzes and diagnoses the event to determine if therapeutic intervention is necessary. If so, the device converts to therapeutic mode, and the control and analysis module activates the therapy module 104*a* for delivery of an appropriate course of therapy in the form of electrical stimulation or chemotherapy. At any or all times, the control and analysis module 102 may activate the communications module 105*a* to interactively communicate the diagnosed cardiovascular event and delivered therapy data to the control and analysis module 102, which combines data received from the communications module to control further operation of the device. The control and analysis module 102 or communications module 105*a* may also electronically communicate 203 the diagnosed cardiovascular event and delivered therapy to an external device like an Advanced Patient Management (APM) system 201 accessible by the patient 200 and/or the physician 202. In this embodiment, the device offers the most flexibility as both a duty cycled device and a device that can prophylactically treat a specific cardiovascular problem upon demand while simultaneously conserving power to extend the device's battery 101 life. By maximizing the duty cycling of the entire device or a specific function of the device, the battery 101 life can be extended to at least 7 years without having to replace the device. Thus, a patient 200 may have to go through the implantation procedure only once during a lifetime.

Figure 5:
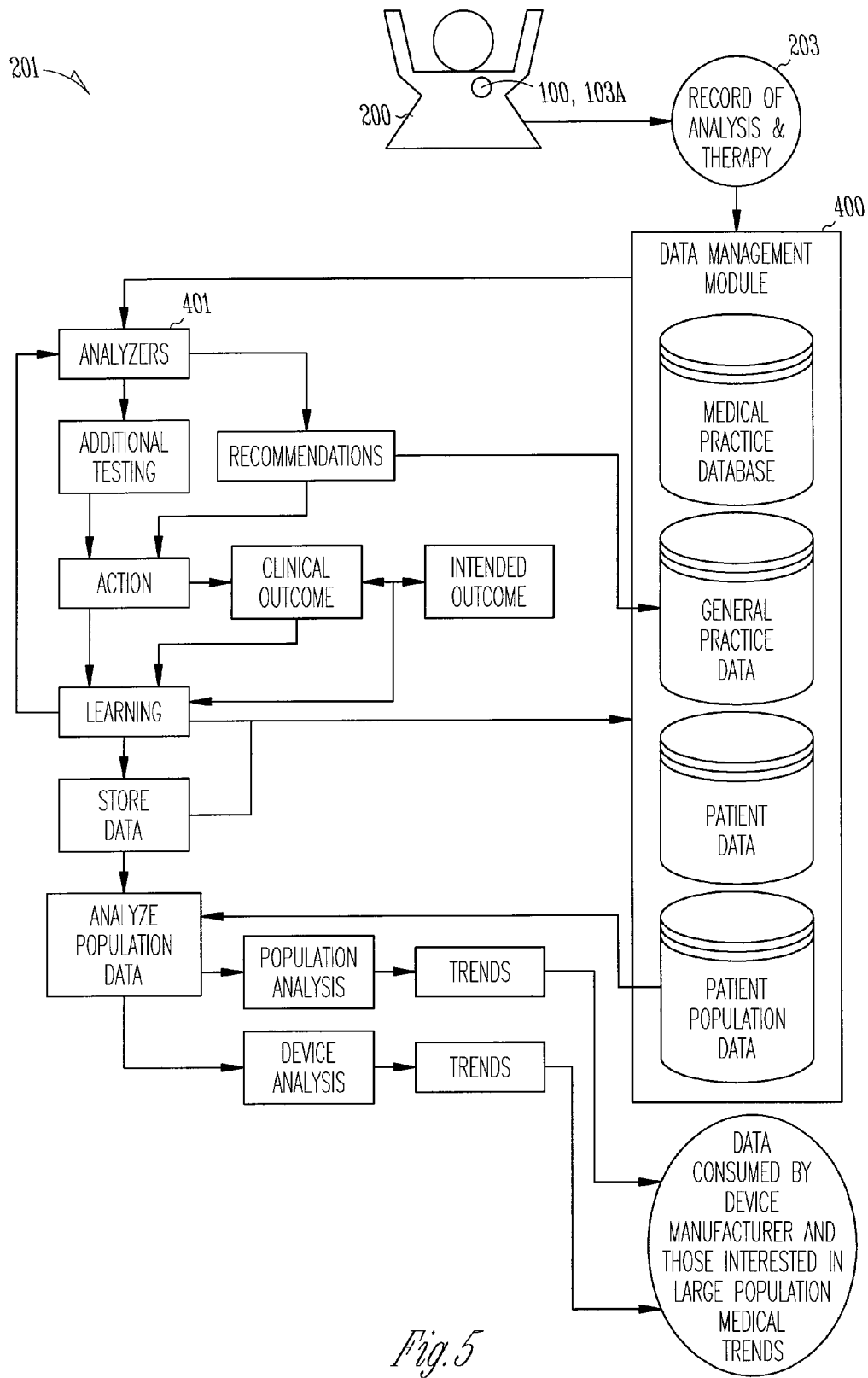
FIG. 5 is a schematic/block diagram illustrating generally, among other things, another embodiment of the convertible, implantable cardiovascular medical device with a controlled diagnostic function of the present invention.

FIG. 5 is a schematic/block diagram illustrating generally another embodiment of the convertible, implantable medical device 100 as a component of an APM system 201. APM is a system that helps patients, their physicians and their families to better monitor, predict and manage chronic diseases. APM is particularly useful in maintaining long-term data continuity and combining information from medical devices, including the device with a controlled diagnostic function disclosed herein, with patient information from other medical databases. In the embodiment shown in FIG. 4, the APM system 201 consists of three primary components: 1) a convertible, implantable medical device 100 including a sensing module 103*a* adapted to monitor physiological functions, 2) a data management module 400 comprising a medical practice database, general practice data, patient data, and patient population data, that processes the data collected from the sensing module, and 3) analyzers 401 that analyzes data from the data management module 400. APM is designed to support physicians and other clinicians in using a variety of different devices, patient-specific and non-specific data, along with medication therapy, to provide the best possible care to patients.

The various embodiments described above are provided by way of illustration only and should not be construed to limit the invention. The above-described embodiments may be used in combination with each other. Those skilled in the art will readily recognize various modifications and changes that may be made to the present invention without following the example embodiments and applications illustrated and described herein, and without departing from the true spirit and scope of the present invention, which is set forth in the following claims and their equivalents. In the appended claims, the terms "including" and "in which" are used as the plain-English equivalents of the respective terms "comprising" and "wherein."

What is claimed is:

1. A system comprising:
   an implantable medical device comprising:
      a therapy circuit;
      a communication circuit configured to communicate information from the implantable medical device to an external patient management system;
      a physiological sensing circuit;
      a first mode, activated at implant, in which power to at least a portion of the physiological sensing circuit is repeatedly turned on and off successively in a power-saving duty cycle, and in which the therapy circuit and the communications circuit are powered off; and
      a second mode, triggered by the physiological sensing circuit having detected a physiological event when on during the first mode, the second mode configured to override the first mode by permanently activating the therapy circuit, without regard to sensing, the therapy circuit configured to permanently provide ongoing therapy after being permanently activated by the second mode, and the second mode configured to activate the communication circuit.

2. The system of claim 1, in which the second mode initiates a communication from the implantable medical device to an external patient management system.

3. The system of claim 1, in which the second mode powers on the communication circuit permanently.

4. The system of claim 1, in which triggering the second mode converts the implantable medical device from a monitoring mode to an intervention and communication mode upon sensing a physiological event comprising a cardiovascular event warranting therapeutic intervention.

5. The system of 1, in which the therapy circuit includes an electrical stimulus control circuit.

6. The system of claim 1, in which therapy circuit includes a chemotherapeutic agent delivery control circuit.

7. The system of claim 1, in which the second mode is triggered by the physiological sensing circuit detecting the physiological event, and in which the physiological event comprises a tachyarrhythmia event.

8. The system of claim 1, in which the second mode is triggered by the physiological sensing circuit detecting the physiological event, and in which the physiological event comprises a bradyarrhythmia event.

9. The system of claim 1, in which the second mode is triggered by the physiological sensing circuit detecting the physiological event, and in which the physiological event comprises a fibrillation event.

10. A method comprising:
placing an implantable medical device in a first mode that is activated at implant, in which power to at least a portion of a physiological sensing circuit is repeatedly turned on and off successively in a power-saving duty cycle, and in which a therapy circuit and a communication circuit are powered off;
detecting a physiological event, using the physiological sensing circuit, while the implantable medical device is operating in the first mode; and
triggering, in response to the detecting of the physiological event, a second mode that overrides the first mode by permanently powering the therapy circuit, without regard to sensing, to permanently provide ongoing therapy after being permanently activated by the second mode, and activating the communication circuit.

11. The method of claim 10, in which the second mode comprises powering on the communication circuit permanently.

12. The method of 10, in which the powering on includes powering on an electrical stimulus control circuit.

13. The method of claim 10, in which the powering on includes powering on a chemotherapeutic agent delivery control circuit.

14. The method of claim 10, in which the triggering the second mode comprises initiating a communication from the implantable medical device to an external patient management system.

15. The method of claim 10, in which triggering the second mode comprises converting the implantable medical device from a monitoring mode to an intervention and communication mode upon detecting the physiological event, and in which the detecting the physiological comprises detecting a cardiovascular event warranting therapeutic intervention.

16. The method of claim 10, in which the triggering the second mode includes triggering in response to detecting a tachyarrhythmia event.

17. The method of claim 10, in which the triggering the second mode includes triggering in response to detecting a bradyarrhythmia event.

18. The method of claim 10, in which the triggering the second mode includes triggering in response to detecting a fibrillation event.

19. The method of claim 10, in which the first mode includes activating the physiological sensing circuit and deactivating the physiological sensing circuit if no physiological event is sensed.

* * * * *

UNITED STATES PATENT AND TRADEMARK OFFICE
CERTIFICATE OF CORRECTION

PATENT NO.         : 7,333,853 B2                                          Page 1 of 1
APPLICATION NO.    : 10/305548
DATED              : February 19, 2008
INVENTOR(S)        : Mazar et al.

It is certified that error appears in the above-identified patent and that said Letters Patent is hereby corrected as shown below:

In column 9, line 17, in Claim 5, after "of" insert -- claim --.

In column 9, line 19, in Claim 6, after "which" insert -- the --.

Signed and Sealed this

Tenth Day of June, 2008

JON W. DUDAS
*Director of the United States Patent and Trademark Office*